(12) United States Patent
Hadimioglu

(10) Patent No.: US 6,622,720 B2
(45) Date of Patent: Sep. 23, 2003

(54) USING CAPILLARY WAVE DRIVEN DROPLETS TO DELIVER A PHARMACEUTICAL PRODUCT

(75) Inventor: Babur B. Hadimioglu, Mountain View, CA (US)

(73) Assignee: Xerox Corporation, Stamford, CT (US)

(*) Notice: Subject to any disclaimer, the term of this patent is extended or adjusted under 35 U.S.C. 154(b) by 37 days.

(21) Appl. No.: 09/739,988

(22) Filed: Dec. 18, 2000

(65) Prior Publication Data
US 2002/0073989 A1 Jun. 20, 2002

(51) Int. Cl.[7] .......................... A61M 11/00; B05B 17/06
(52) U.S. Cl. .......................... 128/200.16; 128/203.12; 128/203.15; 128/203.17; 128/203.26; 128/203.27
(58) Field of Search .................. 128/200.16, 200.21, 128/200.23, 203.12, 203.15, 203.17, 203.26, 203.27

(56) References Cited

U.S. PATENT DOCUMENTS 3,387,607 A * 6/1968 Gauthier et al. ....... 128/200.16
3,433,461 A * 3/1969 Scarpa .................. 239/102.2
4,044,273 A * 8/1977 Kanda et al. ............. 310/335
4,424,465 A * 1/1984 Ohigashi et al. .......... 310/335
4,976,259 A * 12/1990 Higson et al. ......... 128/200.14
5,485,828 A * 1/1996 Hauser ................. 128/200.16
5,803,099 A * 9/1998 Sakuta et al. .............. 134/105
5,855,203 A * 1/1999 Matter .................. 128/207.14
6,014,970 A * 1/2000 Ivri et al. .............. 128/200.14
6,120,449 A * 9/2000 Snyder et al. .............. 600/447
6,182,655 B1 * 2/2001 Keller et al. ........... 128/203.12
6,328,421 B1 * 12/2001 Kojima et al. ................ 347/46

* cited by examiner

Primary Examiner—Weilun Lo
Assistant Examiner—Michael G. Mendoza
(74) Attorney, Agent, or Firm—Kent Chen (57) ABSTRACT

An inhaler that uses capillary effects to output droplets of pharmaceutical product is described. The inhaler includes transducers and lenses to generate focused acoustic waves. The frequency and pulse width output of the transducers are set to cause capillary action in a reservoir of pharmaceutical product. The capillary action results in the ejection of small droplets of pharmaceutical product at low frequencies.

21 Claims, 5 Drawing Sheets

USING CAPILLARY WAVE DRIVEN DROPLETS TO DELIVER A PHARMACEUTICAL PRODUCT

BACKGROUND OF THE INVENTION

Many pharmaceutical products or drugs that provide relief from nasal or lung ailments are delivered through the respiratory system. In order to deliver these drugs, typically, the drug is compressed in a container. Users release the compressed pharmaceutical by opening a valve for a brief interval of time near the user's mouth or nose. Pump mechanisms may also be used to directly spray the pharmaceutical into the user's mouth or nose. The user may then draw a breath to further inhale the pharmaceutical product.

These techniques for delivering pharmaceuticals pose several problems. The first problem is that the droplet size produced is typically too large to be carried in an air stream generated by a normal intake of breath. Thus, in order to transport the larger droplets of pharmaceutical products, the product is propelled into the orifice. This may be done by using compressed air or by expelling the pharmaceutical product into the orifice at a high speed.

Unfortunately, a fast moving particle, defined as a particle that is moving much faster than the accompanying airstream, cannot easily travel around bends that occur in the human respiratory system. Thus, when the traditional means of injecting pharmaceuticals into the mouth are used, much of the pharmaceutical product is deposited on the back of the mouth or in the throat. The deposited pharmaceutical product may then be ingested into the digestive tract instead of the respiratory system. The ingested pharmaceutical product represents lost or wasted medication.

A second problem is that the varying amounts of lost pharmaceutical product makes it difficult to control dosages. Wasted droplets of medication that are deposited on the back of the throat make it possible that the patient will receive insufficient medication Determining the amount wasted and trying to compensate for the wasted medication is a difficult and inexact process.

Thus an improved method and apparatus of delivering pharmaceutical products to a patient's respiratory system is needed.

SUMMARY OF THE INVENTION

An inhaler that uses capillary effects to output droplets of pharmaceutical product is described. The inhaler includes transducers and lenses to generate focused acoustic waves in a reservoir of pharmaceutical product. The frequency and pulse width output of the transducers are set to cause capillary action in the pharmaceutical product. The capillary action results in the ejection of small droplets of pharmaceutical product at low frequencies. The low frequencies used allow more flexibility in the design of the inhaler.

DETAILED DESCRIPTION OF THE INVENTION

An inhaler system that adapts acoustic ink printing technology to output small droplets of pharmaceutical product at a low velocity is described. The droplets are preferably less than 10 micrometers in diameter. Small droplet size and an output speed approximately matching the rate of airflow into the respiratory system maximizes the quantity of medication administered to a patient's lungs.

Figure 1:
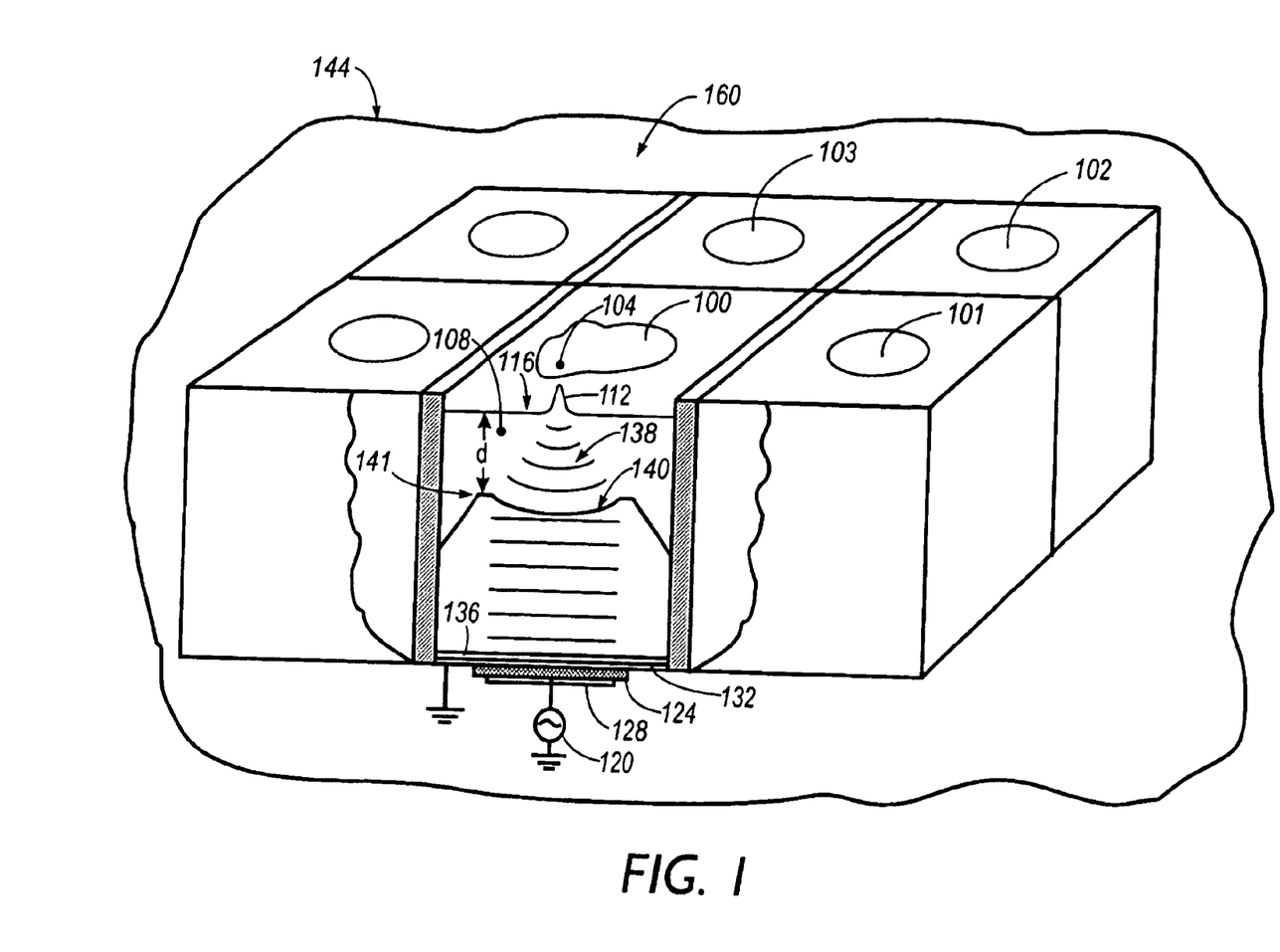
FIG. 1 shows a cross section of a droplet ejector in an array of droplet ejectors ejecting a droplet of pharmaceutical product.

FIG. 1 shows an array 160 of droplet sources such as droplet sources 100, 101, 102, 103 for use in an inhaler 144. Each droplet source 100, 101, 102, 103 is capable of outputting droplets of pharmaceutical product. Inhaler 144 is designed such that the combined output of all droplets sources in array 160 over a predetermined period of time are sufficient to deliver a desired volume of pharmaceutical product to a patient. The pharmaceutical product is typically liquid that contains organic compounds for deposition in the lungs of the patient.

FIG. 1 includes a cross sectional view of one example droplet source 100 in array 160. The cross sectional view also shows a distribution of a reservoir of pharmaceutical product 108 shortly after ejection of a droplet 104 and before a mound 112 on a free surface 116 has relaxed. A radio frequency (RF) source 120 provides a RF drive energy to a driver element such as a transducer, typically a piezoelectric transducer 124, via bottom electrode 128 and top electrode 132. The acoustic energy from the transducer passes through base 136 into an acoustic lens 140. Acoustic lens 140 focuses the received acoustic energy into a focused acoustic beam 138 that terminates in a small focal area near free surface 116. In the illustrated embodiment, each droplet source in array 160 of droplet sources includes a corresponding acoustic lens and transducer to form an array of acoustic lenses and transducers.

Traditional acoustic ink printers usually use RF drives with frequencies of around 100 to 200 Megahertz (MHz). However, when droplet sources are used in inhalers, higher frequencies are preferred because higher frequencies generate smaller droplets that are more easily carried by air currents into the respiratory tract. Droplet sizes are typically on the order of the wavelength of the bulk acoustic wave propagating in the pharmaceutical product. This wavelength may be determined by dividing the velocity of sound for bulk wave propagation in the pharmaceutical product by the frequency of the bulk acoustic wave. Thus by increasing frequency, droplet size can be reduced A RF drive frequency exceeding 300 MHz typically results in the generation of droplets smaller than 5 micro-meters in diameter. Thus inhalers that directly eject droplets preferably operate in frequency ranges exceeding 300 MHz.

Higher frequencies used in inhaler droplet sources also result in higher power losses. Power losses in a droplet source are approximately proportional to the square of the frequency. Power losses in a droplet source are also proportional to the distance "d" from the top surface 141 of acoustic lens 140 to free surface 116 of the pharmaceutical product reservoir. In order to compensate for increased power losses due to the increased operating frequencies, distance "d" may be reduced compared to traditional AIP print heads. In inhaler applications, a distance "d" less than 150 micrometers may be used to conserve power.

A more detailed description of the droplet source or "droplet ejector" operation in a traditional AIP printhead is provided in U.S. Pat. No. 5,565,113 by Hadimioglu et al. entitled "Lithographically Defined Ejection Units" issued Oct. 15, 1996 and hereby incorporated by reference.

Figure 2:
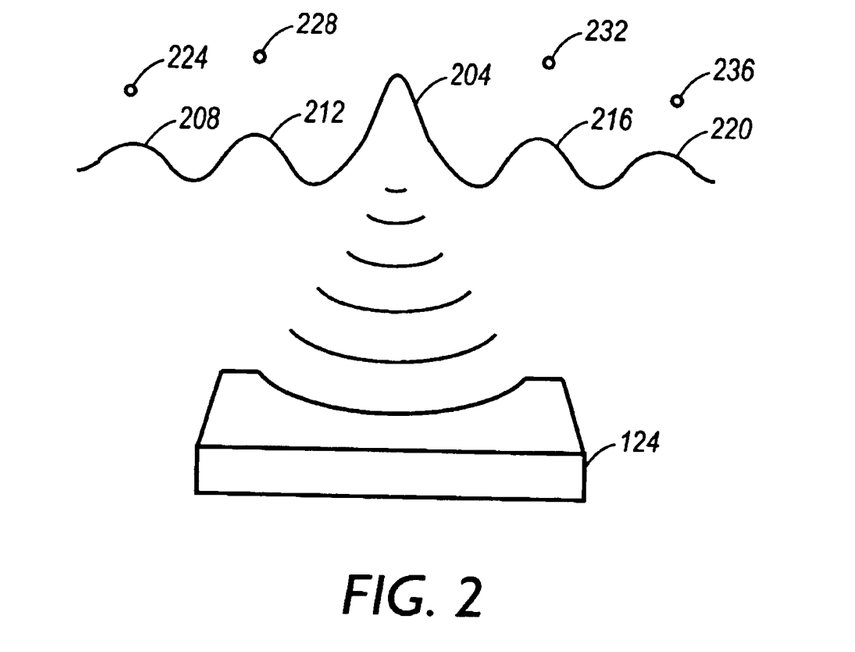
FIG. 2 shows ejection of droplets using capillary action.

FIG. 1 uses focused acoustic energy to directly eject a droplet. FIG. 2 shows an alternative method of generating droplets using capillary action. When generating capillary wave-driven droplets, the principle mound 204 does not receive enough energy to eject a droplet. Instead, as the principle mound 204 decreases in size, the excess liquid is absorbed by surrounding capillary wave crests or side mounds 208, 212, 216, 220. These wave crests eject a mist corresponding to droplets 224, 228, 232, 236. In order to generate capillary action droplets instead of focused, single ejection droplets, each ejector transducer generates shorter pulse widths at a higher peak power. Example pulse widths are on the order of 5 microseconds or less when the transducer provides a peak power of approximately one watt or higher per ejector.

One advantage of using capillary action is the lower frequencies that can be used to create smaller droplets. The diameter of capillary generated droplets is similar in magnitude to the wavelength of capillary waves. The wavelength of capillary waves can be determined from the equation: wavelength=$[2*Pi*T/(ro*f^2)]^{(1/3)}$ wherein T is the surface tension of the pharmaceutical fluid, ro is the density of the pharmaceutical fluid and f is the frequency output of the transducer. This equation and a more detailed explanation are provided on page 328 of Eisenmenger, *Acoustica*, 1959 which is hereby incorporated by reference. At typical densities and surface tensions, frequencies of 10 Megahertz (MHz) generate a capillary wavelength of 1.5 micrometers and a frequency of 1 MHz generates a capillary wavelength of 6.8 micrometers. Thus it is possible to generate approximately 5 micrometer diameter droplets at RF frequencies about two orders of magnitude smaller than the bulk waves used to generate "conventional" AIP droplets.

In capillary wave droplet systems, the lower frequencies used allows more flexibility in materials and tolerances used to fabricate transducers and acoustic lenses used to form the array of droplet sources. For example, plastics are not as lossy at the lower frequencies. The lower loss levels allow relatively inexpensive molded plastic spherical lenses to be used as acoustic lenses.

Figure 3:
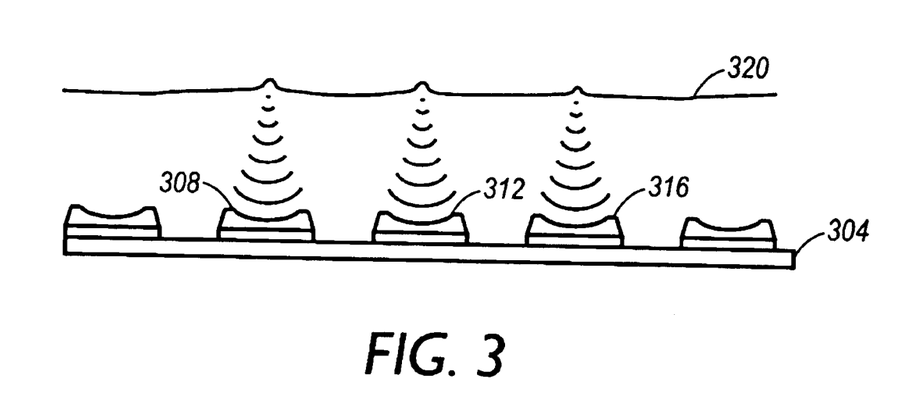
FIG. 3 shows one embodiment of forming an inhaler that uses a single transducer to drive multiple droplet sources.

A second method of minimizing the cost of fabricating an array of droplet sources is to replace the plurality of transducers with a single transducer, the energy from the single transducer distributed to multiple lenses corresponding to multiple droplet sources. FIG. 3 shows an example of such a single transducer structure. In FIG. 3, each droplet source corresponds to an acoustic lens such as acoustic lenses 308, 312, 316. The acoustic lenses are positioned over a single large transducer 304. Each acoustic lens independently focuses a portion of the bulk planar wave produced by single large transducer 304 to create droplets across a free surface 320. Using a single transducer instead of the multiple transducers shown in FIG. 1 substantially reduces the cost associated with multiple transducers and the electronics to drive multiple transducers.

The number of droplet sources in an array of droplet sources may vary and typically depends on the dosages that will be administered. A typical five micron diameter drop of pharmaceutical product contains about 0.07 picoliters of fluid. Assuming a repetition rate of 200 Khz, a rate easily achievable with the typical ejector, each droplet source will deliver approximately 14 microliters per second. To administer medication at the rate of 100 milliliters per second, a typical number of ejectors may be around 7,000.

Figure 4:
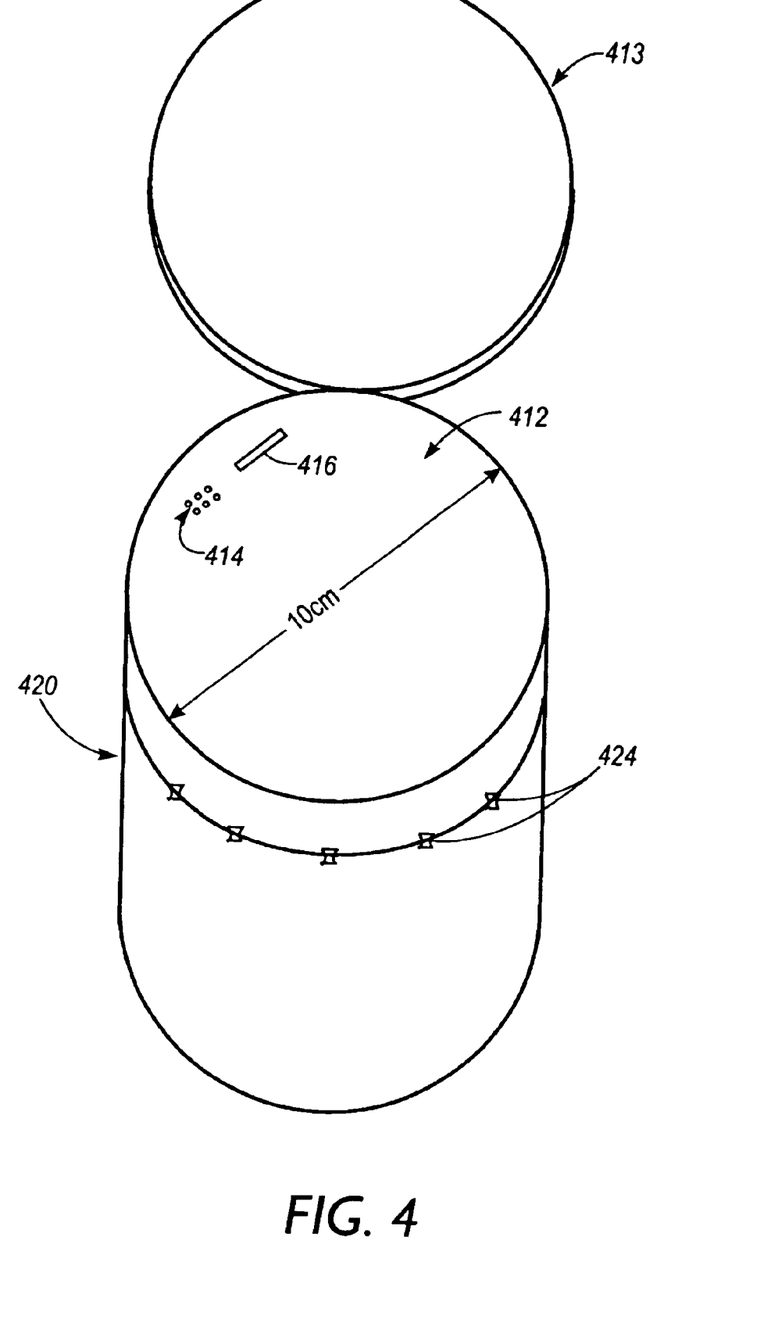
FIG. 4 shows an example distribution of droplet ejectors on an inhaler head.

FIG. 4 shows a top view of an example distribution of droplet sources. Typically, the droplet sources are mounted on a circular head 412 over a distance of approximately 10 centimeters to facilitate insertion into an oral cavity. Alternative configurations of droplet sources may be designed for insertion into a nasal cavity. Although a circular pattern of droplet sources best utilizes the surface area of circular head 412, in high viscosity pharmaceutical products, the flow of the product evenly across a circular pattern may prove difficult. Thus, in an alternate embodiment, a more linear pattern of droplet sources may be used.

Prevention of contamination, both from airborne particulate matter as well as organic matter such as bacteria is an important concern with the inhaler. Typically, openings 414 in circular head 412 are substantially larger than the droplet size ejected. For example, a typical opening size for ejection of a 10 micron diameter droplet may be approximately 100 microns. When droplet sources are not activated, the pharmaceutical product is maintained within the circular head 412 via surface tension across opening 414. The relatively large exposed surface area of opening 414 may allows dust and other particulate matter to enter the openings and contaminate the pharmaceutical product.

A cover 413 that fits over the circular head 412 helps minimize particulate contamination. In one embodiment opening and closing cover 413 may switch on and off the inhaler. An alternate method of avoiding contamination uses micro electro-mechanical structure (MEMS) covers 416 positioned over each opening. MEMS cover 416 may open for a short time interval allowing droplets to be ejected and remain closed during other time periods. In one embodiment, the cover, whether a large area cover or a MEMS covers, may be electronically controlled such that the ejection of droplets causes the cover to automatically retract out of the path of the ejected droplets. Such electronic control may be achieved by synchronizing a cover control with the electrical impulse driving the transducers.

Besides particulate contamination, bacterial contamination should also be minimized. One method of controlling bacterial contamination is to regularly sterilize the ejector head using UV radiation. However, may patients do not have the discipline to regularly sterilize the ejector head. One method of forcing a regular sterilization schedule is to automatically expose the ejector heads to UV radiation whenever the inhaler power supply is being recharged.

Often, even with sterilization and covers, some contamination of the ejector heads over time is inevitable. Furthermore, when fresnel zone plates are used as acoustic lenses, the ejector may be hard to clean making it difficult to use the same ejector head with several different medications. Plastic spherical lenses are easier to clean and can be used at lower frequencies, such as are typically associated with a capillary action droplet ejector. In systems where several different medications are being administered or where the ejector becomes otherwise contaminated, the ejector head 420 detaches from a body of the inhaler and can be replaced by a replacement head or a disposable ejector head. A clip-on or other fastener mechanism 424 attaches ejector head 420 to the body. In one embodiment of the invention, an ultraviolet (UV) radiation source 422 sterilizes ejector head 420.

FIG. 5 shows a cut away side view of one embodiment of inhaler 500 including ejector head 504 and handle 508.

A typical ejector uses approximately two nanojoules of acoustic energy at the liquid surface per drop of liquid ejected. Multiplying the power needed at the liquid surface by the loss factor of the ejector results in an approximate power requirement of 20 nanojoules per ejector at the ejector head. The total power used is calculated by multiplying the power per ejector at the ejector head by the total number of ejectors. To deliver a 100 microliter dose five times a day, the total power requirement is approximately 140 joules which is well within the power capabilities of most batteries, including most rechargeable nickel/cadmium batteries.

Figure 5:
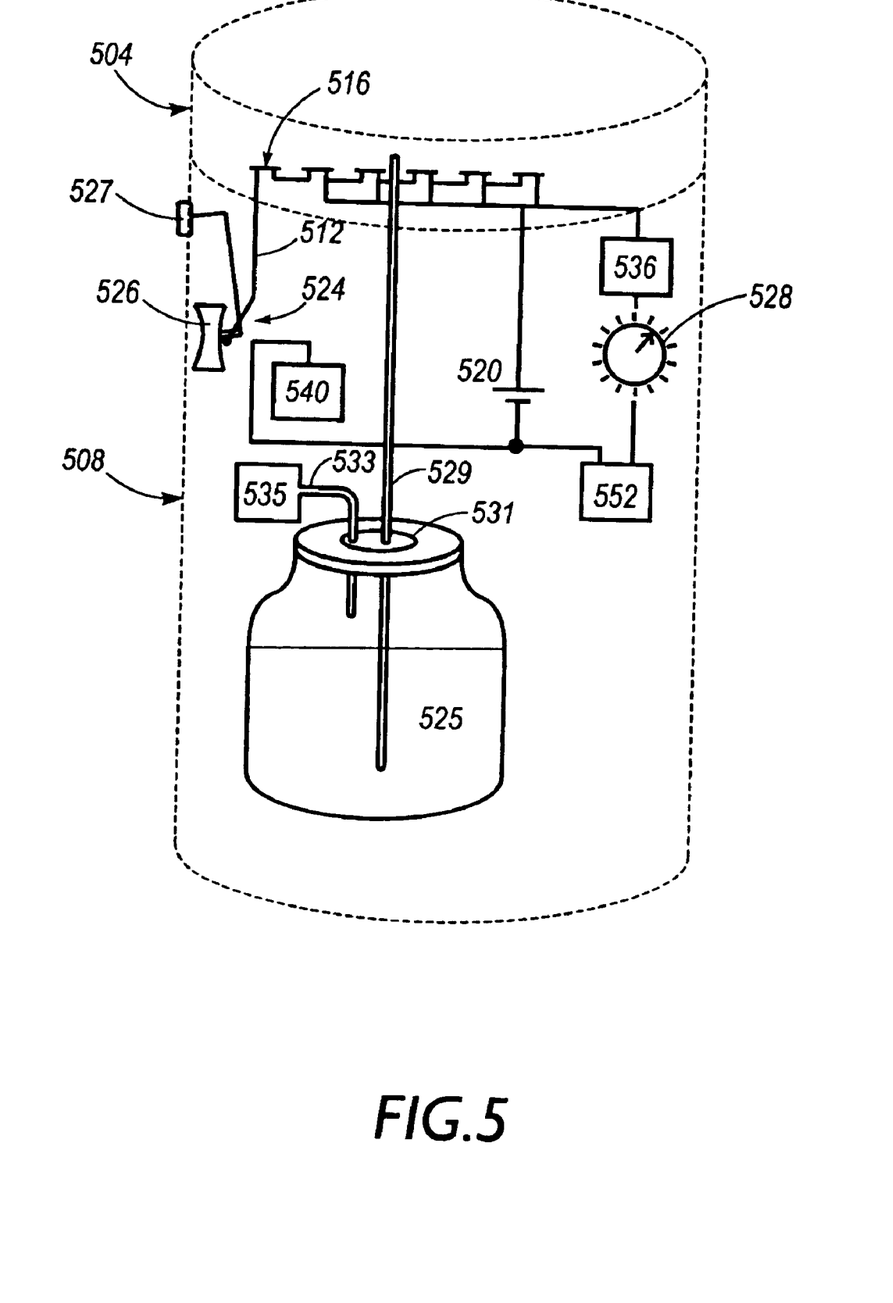
FIG. 5 shows a cross sectional side view of one embodiment of an inhaler designed for insertion into the mouth of a patient.
Figure 6:
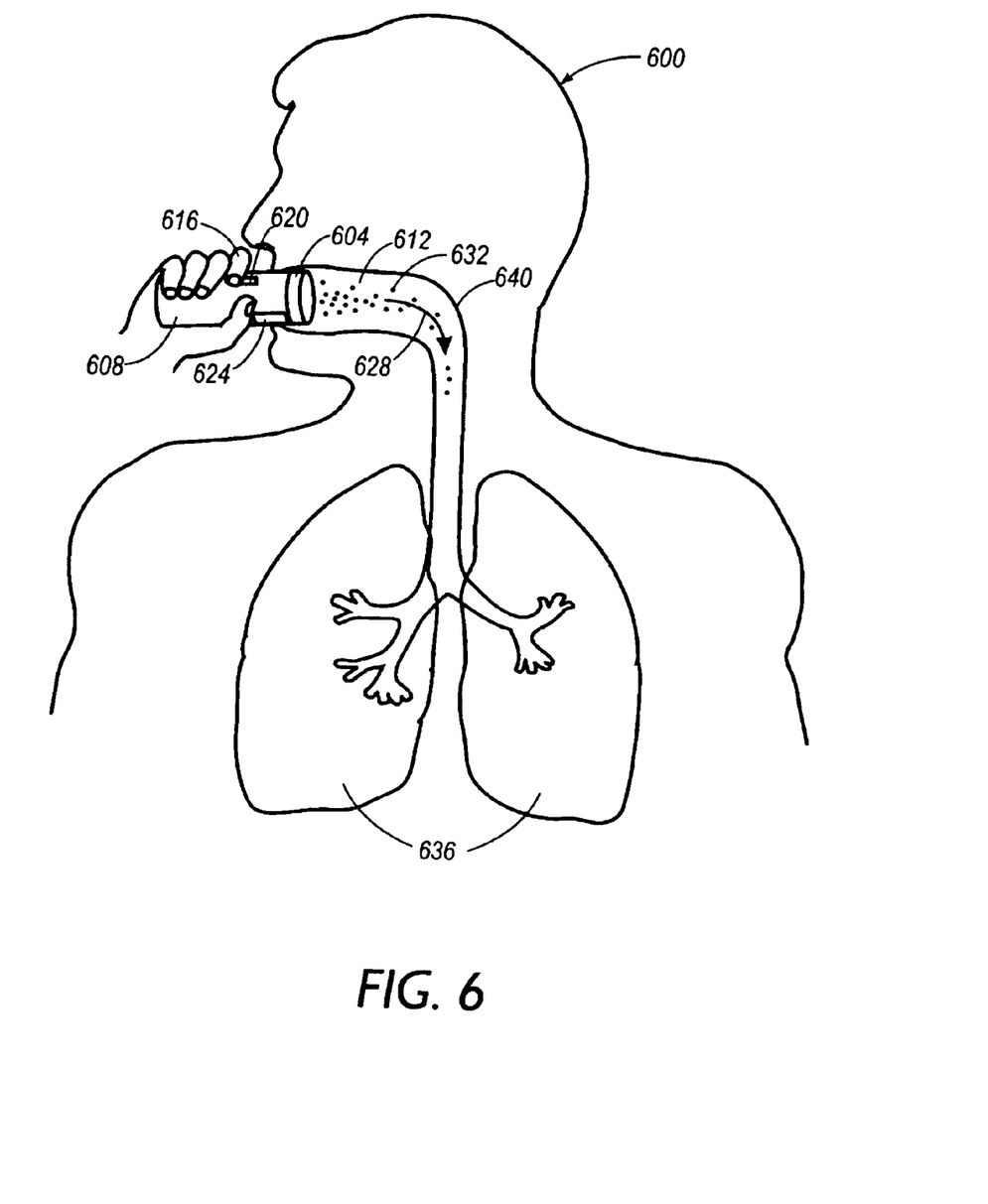
FIG. 6 shows the inhaler in use by a patient.

In one embodiment of the invention, a handle 508 of the AIP inhaler includes a container that stores a reservoir 525 of medication. When the ejector head is attached to the inhaler body, a pipe 529, typically a hypodermic needle punctures a seal 531 that seals the reservoir 525 of medication. Typically, seal 531 is a rubber gasket that covers a section of the container of medication. A second pressurization needle 533 also punctures the rubber gasket and pumps gas into reservoir 525 slightly pressurizing the medication. The applied pressure should be sufficient to force the medication up pipe 529; however, the pressure should not be excessive such that it breaks the surface tension at the openings of the ejector head. Breaking the surface tension will prematurely force medication from the openings of the ejector head. Pressure detection system 535 monitors the pressure differential between the ambient surroundings and the pressure inside reservoir 525 and maintains the desired pressure to keep fluid in the ejector head without breaking the surface tension of each opening.

When drops are to be ejected, ejection switch 524 is closed. Closing ejection switch 524 activates the ejectors on ejector head 504 for a predetermined time interval. In one embodiment the invention, switch 524 is a trigger 526. After the droplet ejectors are placed in close proximity to an oral cavity, a patient presses trigger 526 closing of switch 524. Closing switch 524 cause the ejection of medication. In a second implementation of a switch control, an airspeed detector 527 controls the closing of switch 524. In particular, when an inhalation by the patient causes the speed of air around the ejectors to approximately match the expected speed of ejected droplets, the airspeed detector closes switch 524. The matched air speed provides an optimal air current for carrying droplets from the ejector into a patient's lungs.

Dosage setting switch 528 allows the user to adjust the dosage of medication provided by adjusting the duration of ejector operation after switch 524 is closed. In the illustrated embodiment, dosage setting switch 528 controls timer 532. Timer 552 determines a time duration over which power is provided to piezoelectric 516. The time interval is typically proportional to the dosage set on dosage setting switch 528. When all ejectors are fired, the time interval is typically the dosage divided by the total output of ejectors on ejector head 504 per unit time.

When small dosages are desired, the dosage setting switch 528 may be programmed to reduce the number of ejectors fired on ejector head 504 by adjusting a control signal from control circuit 540. The control signal switches ejectors in drive circuit 536. Reducing the number of ejectors fired reduces the output of pharmaceutical product per unit time. The duration of ejector firing may also be selected based on the droplet ejector switching mechanism. When an airspeed detector 527 is used, extension of the pharmaceutical discharge time may be undesirable. Instead, it may be desirable to maximize the ejection of droplets during a very short time interval to take advantage of the optimal air speed, thus typically all ejectors will fire for a fraction of a second. However, in trigger based or manual operation, it may be desirable to extend the time interval slightly to allow for imprecise synchronization between ejection of droplets and inhalation.

Drive circuit 536 provides the drive signal to the ejectors on ejector head 504. In a simple implementation of drive circuit 536, all ejectors are simultaneously activated. Thus, in one embodiment of the invention, all ejectors may be connected in parallel such that closing switch 524 results in simultaneous ejection of droplets from all ejectors. However, circumstances may dictate that all ejectors not be fired at once. For example, when power source 520 is low on energy and needs recharging, the electric current provided may be insufficient to fire all ejectors simultaneously. In such cases, the drive circuit may detect the lower power output and fire different ejectors at different times or switch some ejectors off altogether with a corresponding increase in time duration to allow dispensing of the recommended dosage. As previously described, a request for a very low dosage may also result in firing of less than all of the ejectors at once. System design my also dictate that not all ejectors are fired at once. Typically, RF power is power is switched on to a group of ejectors for a time duration, on the order of microseconds, and then switched off for several microseconds. In order to minimize the peak power requirements of the inhale when the RF power is switched off to the group of ejectors, a second group of ejectors may receive RF power. Thus a multiplexing circuit may alternately switch groups of ejectors on and off and avoid overlapping firing times.

FIG. 6 illustrates the use of the inhaler by a human subject. In the illustrated embodiment, the patient 600 inserts the applicator or ejector head 604 of the inhaler 608 into an oral cavity 612. After insertion of inhaler 608, a finger such as a pointer or trigger finger 616 applies pressure to a switch 620. Alternately, the inhalation of air causes an airspeed indicator to detect the airspeed in aperture 624 and trigger a switch when the airspeed reaches a desired value. Under either implementation, the switch closes at a particular point in time causing power to be provided to the ejectors for a preset time duration and the ejection of a mist of medication into oral cavity 612.

As the mist of medication is produced, the patient deeply inhales. The inhalation causes air currents 628 to carry the droplets 632 of pharmaceutical product to the patient's lungs 636 where the pharmaceutical product is absorbed. The matching of the ejection speed of droplets 632 with the speed of air currents 628 and the small size of droplets 632 maximizes the percentage of pharmaceutical product that reaches lungs 636 and minimizes the percentage of pharmaceutical product deposited on the back of the throat 640.

While the preceding invention has been described in terms of a number of specific embodiments, it will be evident to those skilled in the art that many alternatives, modifications and variations may be performed while still remaining within the scope of the teachings contained herein. For example, specific power consumption of ejectors, ejector arrangements, methods of switching on the ejectors and methods of maintaining sterility of the inhaler have been described. However, such details should not be used to limit the scope of the invention and are merely provided to serve as examples for performing the claimed invention and lend clarity to the description. Accordingly, the present invention should not be limited by the embodiments used to exemplify it, but rather should be considered to be within the spirit and scope of the following claims and its equivalents, including all such alternative, modifications and variations.

What is claimed is:

1. A portable apparatus for delivering a pharmaceutical product comprising:
   a plurality of driver elements, the plurality of driver elements including at least three driver elements to generate acoustic energy;
   a plurality of acoustic lenses to focus the acoustic energy generated by the plurality of driver elements;
   a delivery system to maintain the pharmaceutical product in a position to receive the acoustic energy from the acoustic lens and cause ejection of a droplet of pharmaceutical product; and, a housing surrounding said plurality of driver elements, the plurality of acoustic lenses and the delivery system, the housing including a section that includes a plurality of apertures for insertion into a human orifice, the apertures to allow delivery of a measured dose of pharmaceutical product into the human orifice.

2. The apparatus of claim 1 further comprising:

a source of electrical power coupled to the plurality of driver elements.

3. The apparatus of claim 1 wherein the plurality of acoustic lenses are fresnel lenses.

4. The apparatus of claim 1 wherein the plurality of acoustic lenses are plastic spherical lenses.

5. The apparatus of claim 1 wherein the section for insertion into a human orifice is approximately sized to fit into a human mouth.

6. The apparatus of claim 1 further comprising:

a portable energy source to provide energy to the plurality of driver elements.

7. The apparatus of claim 6 further comprising:

a multiplexing circuit that directs RF energy from the portable energy source to a second driver element only when energy is not provided by the portable energy source to a first driver element.

8. The apparatus of claim 1 wherein the plurality of driver elements are programmed to generate acoustic energy in pulses that are of a short duration and low frequency such that droplets of pharmaceutical product are output due to capillary action.

9. The apparatus of claim 8 wherein the plurality of driver elements are programmed to output acoustic energy at a frequency below 15 MHz.

10. The apparatus of claim 9 wherein the droplets of pharmaceutical product output due to capillary action are less than 10 micrometers in diameter.

11. The apparatus of claim 1 wherein the delivery system further comprises:

a pressurization system that controls the pressure of the pharmaceutical product.

12. The apparatus of claim 1 further comprising:

a sterilization mechanism that outputs ultraviolet energy to sterilize the plurality of acoustic lenses.

13. The apparatus of claim 1 further comprising:

at least one MEMS cover to protect the plurality of driver elements from contamination when the drivers are not outputting acoustic energy.

14. The apparatus of claim 1 wherein the section for insertion into a human orifice is approximately sized to fit into a nostril of a human nose.

15. A portable to output pharmaceutical product for inhalation into the respiratory system of a patient, the apparatus comprising:

a portable energy supply;

at least three transducers coupled to the portable energy supply, the at least three transducers to output acoustic energy;

a plurality of lenses to receive and focus energy from the at least three transducers;

a delivery system to maintain a reservoir of pharmaceutical product, the reservoir of pharmaceutical product to receive energy from the plurality of lenses the received energy to cause ejection of a plurality of droplets; and, a housing surrounding said plurality of driver elements, the plurality of acoustic lenses and the delivery system, the housing including a section that includes a plurality of apertures for insertion into a human orifice, the apertures to allow delivery of a measured dose of pharmaceutical product into the human orifice.

16. The apparatus of claim 15 wherein each lens in the plurality of lenses is a Fresnel lens.

17. The apparatus of claim 15 wherein each lens in the plurality of lenses is a spherical plastic lens.

18. The apparatus of claim 15 further comprising:

a circuit that detects a flow of air going into a patient's lungs and couples the transducer to the portable energy supply when a critical air speed is reached.

19. The apparatus of claim 15 wherein a distance from a top surface of a lens and a surface of the reservoir of pharmaceutical product is less than 150 micro meters.

20. The apparatus of claim 15 wherein the section for insertion into a human orifice is approximately sized to fit into a human mouth.

21. The apparatus of claim 15 wherein the section for insertion into a human orifice is approximately sized to fit into a human mouth.

* * * * *

UNITED STATES PATENT AND TRADEMARK OFFICE
CERTIFICATE OF CORRECTION

PATENT NO. : 6,622,720 B2 Page 1 of 1
APPLICATION NO. : 09/739988
DATED : September 23, 2003
INVENTOR(S) : Babur B. Hadimioglu It is certified that error appears in the above-identified patent and that said Letters Patent is hereby corrected as shown below:

Title Page, left hand column, line 2, item (12); under "United States Patent" please replace the following:

"Hadimioglu" with --Hadimioglu et al.--

Title Page, left hand column, line 9, item (75); under "Inventor" please add the following after "Babur B. Hadmioglu, Mountain View, CA (US)":

--; Jaan Noolandi, Mississauga, Ontario (CA); Robert A. Sprague, Saratoga, CA (US)--

Signed and Sealed this

Twenty-first Day of October, 2008

JON W. DUDAS
*Director of the United States Patent and Trademark Office*